(12) United States Patent
Berend et al.

(10) Patent No.: US 9,498,339 B2
(45) Date of Patent: Nov. 22, 2016

(54) DEFORMING IMPLANT-BONE INTERFACE (71) Applicant: Biomet Manufacturing, LLC, Warsaw, IN (US)

(72) Inventors: Keith R. Berend, Columbus, OH (US); Kirk J. Bailey, Rochester, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 105 days.

(21) Appl. No.: 14/072,446

(22) Filed: Nov. 5, 2013

(65) Prior Publication Data

US 2015/0127112 A1    May 7, 2015

(51) Int. Cl.
*A61F 2/40* (2006.01)
*A61F 2/38* (2006.01)
*A61F 2/34* (2006.01)
*A61F 2/30* (2006.01)

(52) U.S. Cl.
CPC ............. *A61F 2/34* (2013.01); *A61F 2/389* (2013.01); *A61F 2002/30072* (2013.01); *A61F 2002/30451* (2013.01); *A61F 2002/30583* (2013.01); *A61F 2002/30593* (2013.01); *A61F 2002/30769* (2013.01); *A61F 2002/3438* (2013.01); *A61F 2310/00023* (2013.01); *A61F 2310/00029* (2013.01)

(58) Field of Classification Search
CPC ............. A61F 2/34; A61F 2002/3438; A61F 2002/30072; A61F 2002/30583
See application file for complete search history.

(56) References Cited

U.S. PATENT DOCUMENTS

| | | | | |
|---|---|---|---|---|
| 8,888,861 | B2 * | 11/2014 | Preuss | A61F 2/34 623/22.24 |
| 2004/0267374 | A1 * | 12/2004 | Friedrichs | A61F 2/32 623/22.15 |
| 2013/0079887 | A1 * | 3/2013 | Grostefon | A61F 2/34 623/22.24 |

FOREIGN PATENT DOCUMENTS

EP    1302181    4/2003

* cited by examiner

*Primary Examiner* — Brian Dukert
(74) *Attorney, Agent, or Firm* — Schwegman Lundberg & Woessner, P.A.

(57) ABSTRACT

A prosthesis can have a wall portion that deforms to conform to a surface. The deformation of the wall can be plastic (i.e. permanent) or elastic (i.e. able to return to the pre-deformed configuration). The surface can be an anatomical surface.

15 Claims, 5 Drawing Sheets

DEFORMING IMPLANT-BONE INTERFACE

FIELD

The subject disclosure relates to implants, and particularly to implants with at least one deformable surface.

BACKGROUND

This section provides background information related to the present disclosure which is not necessarily prior art.

When implanting a prosthesis, a prosthetic member can be positioned against a hard, such as a boney, portion of an anatomy. The anatomy can be of any appropriate subject, such as a human patient or an animal patient. Generally, the boney portion is prepared for receiving the prosthetic member by forming the bone to substantially precisely fit or conform to the shape of the preformed prosthetic member. This requires removal of bone mass of the subject. For example, an acetabulum can be reamed with an acetabular reamer to form a curved void to receive an acetabular prosthesis.

SUMMARY

This section provides a general summary of the disclosure, and is not a comprehensive disclosure of its full scope or all of its features.

A prosthetic implant can be positioned in the anatomy to replace a portion of an anatomy. The anatomy may be of any appropriate subject, such as a human subject, an animal subject, or any selected subject anatomy. Additionally, a subject includes any portion or member into which a prosthesis or replacement member may be positioned.

The prosthetic member can be positioned in an anatomy in a generally non-smoothly prepared, partially prepared, or unprepared region. For example, an acetabular prosthesis can be positioned into an acetabulum that is reamed to a non-smooth or non-completely reamed surface. An acetabulum can be prepared without requiring an excessive removal of natural bone or tissue portions of the anatomy and a prosthesis can be positioned within the partially prepared acetabulum to replace the natural acetabulum. Thus, rather than completely reaming an acetabulum to form a substantially curved or hemispherical surface, an acetabular prosthesis can be positioned into an acetabulum where only the diseased or boney portions have been removed. The acetabular prosthesis can then have a wall portion that deforms to conform to the acetabular surface. The deformation can be plastic (i.e. permanent) or elastic (i.e. able to return to the pre-deformed configuration).

Additionally, prosthetic members can be positioned in or adjacent to and in contact with any appropriate anatomical portions, such as a proximal tibia, proximal femur, glenoid, or other appropriate anatomical surface. Generally, the anatomical surfaces, which can generally include boney surfaces, need not be completely reamed or smooth while still allowing for appropriate contact and connection of the prosthetic member with the anatomy. At least one surface of the prosthetic member may deform to match or conform to the boney surface.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
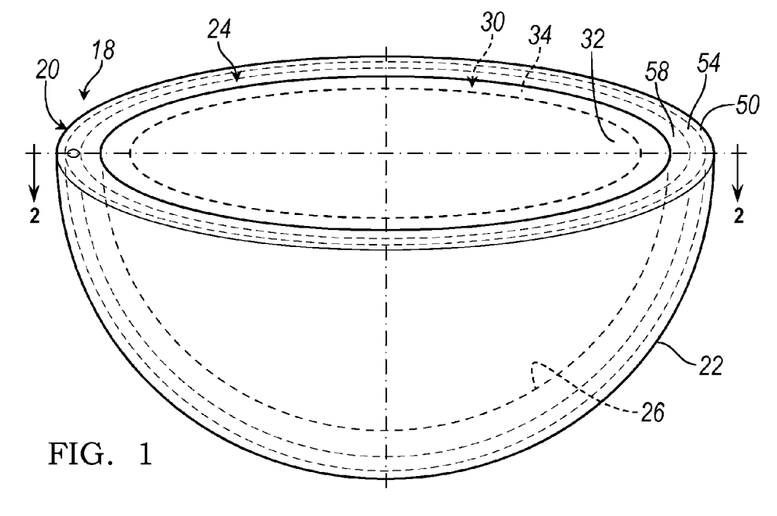
FIG. 1 is a perspective view of an acetabular prosthesis assembly, according to various embodiments.

With reference to FIG. 1 an acetabular prosthesis assembly 18 is illustrated. The acetabular assembly 18 can include an acetabular shell or cup 20. The acetabular prosthesis assembly 18 and/or cup 20 can be similar to any generally available prosthesis such as the Ringloc® acetabular prosthesis, sold by Biomet, Inc. having a place of business in Indiana, United States. The acetabular prosthesis can generally include an exterior surface 22 an upper rim 24 and an interior surface 26. Positioned within the interior surface 26 can be a bearing member or prosthetic portion 30. The bearing member 30 can include an internal articulating surface 32 and an upper rim 34. The design of the acetabular bearing 30 can be similar to the design of the bearing member of the acetabular prosthesis, as discussed above.

The exterior surface 22 can have a substantially curved surface, and may be substantially hemispherical, according to various designs. Additionally, the exterior surface 22 can have a boney ingrowth portion, such as a porous titanium or other porous metal construct, including Regenerex® porous metal sold by Biomet, Inc. Additionally, a plasma coating or other porous coating can be provided on the exterior surface 22 of the acetabular prosthesis 20. Further, screw holes or other fixation features can be provided to interconnect the acetabular prosthesis 20 with the selected subject. Various implantation and fixation mechanisms will not be described in detail here.

Figure 2:
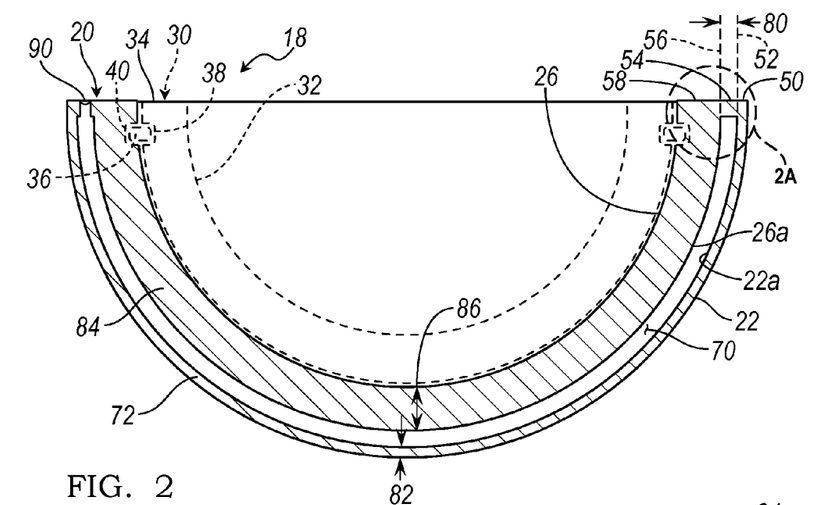
FIG. 2 is a cross-section of the acetabular prosthesis assembly of FIG. 1 taken along the line 2-2.

With continuing reference to FIG. 1 and additional reference to FIG. 2, the acetabular prosthesis 20 can be formed such that the bearing member 30 is fixed within the inner or relative to the inner surface 26 via a ring locking member 36 that is received within a first groove 38 of the bearing member 30 and a second groove 40 of the prosthesis 20. The second groove 40 can be formed in the surface 26 of the prosthesis member 20 in an appropriate location relative to the upper rim 24.

The upper rim 24 can be formed to have a plurality of regions extending between the exterior surface 22 and the interior surface 26. For example, a first or exterior region 50 of the upper rim 24 can extend between the exterior surface 22 of the prosthesis 20 and a first boundary or region 52 that is generally defined by an internal wall surface 22a of the prosthesis 20. A second region 54 can extend from the first boundary 52 to a second boundary 56 that is generally defined by a second internal surface 26a of the prosthesis 20. An internal or third region 58 can extend from the second boundary 56 to the internal surface 26 of the prosthesis 20. Defined between the first inner surface 22a and the second inner surface 26a can be a void or opening 70. The void 70 can be substantially enclosed by the prosthesis 20 between the external surface 22 and the internal surface 26, and at least a portion of the upper rim wall 24. The void 70 defines an open area or void area into which an outer wall 72, that defines the surfaces 22, 22a can compress or deform into, as discussed further herein.

The upper rim wall 24, including the second region 54, is generally substantially rigid. The rigid upper rim wall 24, including the middle or intermediate region 54 can include appropriate thickness or other physical property or feature so that it will not substantially deform during implantation and positioning of the prosthesis 20 within a subject. As discussed herein, the outer wall 72 can deform into the void 70, but the upper rim wall 24 will remain substantially rigid such that the upper rim wall 24 does not deform. The void 70 can include any appropriate dimension, for example, a dimension 80 that extends between the first region 42 and the second region 56. The outer wall 72 can further include a thickness 82 that can allow the outer wall 72 to deform into the void 70, as discussed further herein. The prosthesis 20, therefore, can further include an internal wall 84 that defines the inner surface 26 and includes a thickness 86. Generally, the thickness 82 of the outer wall 72 is less than the thickness 86 of the inner wall 84. However, it is understood, that the thickness 82 of the outer wall 72 can be substantially equivalent or identical to the thickness 86 of the inner wall 84.

The acetabular prosthesis 20 can be formed of various materials, such as appropriate biocompatible metals. For example, titanium and cobalt-chromium alloys can be used to form the acetabular prosthesis 20. Additionally, the prosthesis member 20 can be formed of an appropriate polymer material to be positioned within the anatomy. Appropriate bearing materials can be used for the bearing member 30, such as high molecular weight polyethylene that is formed into a selected shape to be positioned within the prosthesis 20. The inner surface 26 can be formed to appropriately receive the bearing member 30, such as being formed with a highly polished or mirrored polished surface.

The various thicknesses, such as the thickness of the outer wall 72 and the inner wall 84 can vary depending upon the material selected for forming the prosthesis 20. The thickness of the outer wall 72 is generally selected to allow for deformation by contact with bone and a force provided by a user, such as a human surgeon. Thus, the thickness is generally selected to allow for a user to deform the outer wall 72. For example, a prosthesis having an outer wall formed of titanium may have the outer wall 72 have a thickness 82 of about 0.25 millimeters (mm) to about 1.0 mm. The inner wall 84 can have the thickness 86 of about 2.5 mm to about 4 mm. The dimension of the void 70, such as the dimension 80 near the upper rim 24 can include a dimension of 0.5 mm to about 1.5 mm to allow for an appropriate amount of deformation of the outer wall 72 during implantation.

The prosthesis 20 can further include an opening or connection 90 that can be formed in any appropriate configuration to allow for connection of a supply device 250 (FIG. 6), such as a syringe. The supply device 250 can supply an appropriate material into the void 70. Appropriate materials can include hardening materials, such as polymerizing or polymerizable materials. The material can fill the void 70 to provide additional rigidity to the outer wall 72 at a selected point in time. The material can fill the void 70 to provide for physical contact between the first surface 22a and the second surface 26a.

Figure 2A:
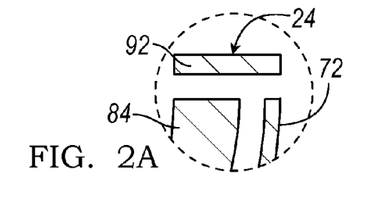
FIG. 2A is a detailed exploded view taken within circle 2A of FIG. 2.

With continued reference to FIG. 2 and additional reference to FIG. 2A, the prosthesis 20 can be formed in any appropriate manner. For example, the exterior wall 72 and interior wall 84 can be formed as two separate members that are interconnected with a top wall 92, which is also separate from the exterior wall 72 and the interior wall 84, that forms the upper rim 24. The three wall portions 72, 84 and 92 can be interconnected within an appropriate connection mechanism including welding, adhesives, brazing, spin welding, or other appropriate mechanism. Accordingly, each separate portion of the prosthesis 20 can be formed separately according to appropriate manufacturing techniques, with selected dimensions, physical properties, and/or various materials. For example, as discussed above, the exterior wall 72 can be formed to deform during implantation and positioning of the prosthesis 20. Accordingly, the exterior wall 72 can be formed of a material that is different than the interior wall 84 and/or the upper wall 92. Furthermore, each of the wall portions can be formed at different thicknesses, plurality of thicknesses for each of the wall portions, or other appropriate dimensions or physical properties.

It is also understood that the interconnection of the wall members can occur at any appropriate time, such as during manufacturing of the prosthesis 20 such that the prosthesis 20 is provided to a user, such as a surgeon, as a single connected member or piece. Nevertheless, each of the wall portions, 72, 84, and 92 can be formed separately and interconnected. In addition, it is understood that the upper wall 92 can be formed integrally as a single piece with either one of the inner wall 94 or the exterior wall 72 and only the other wall connected to the appropriate wall 92. Thus, the prosthesis 20 can be formed of a plurality of pieces including three pieces, two pieces, or formed as a single one piece member.

Figure 3:
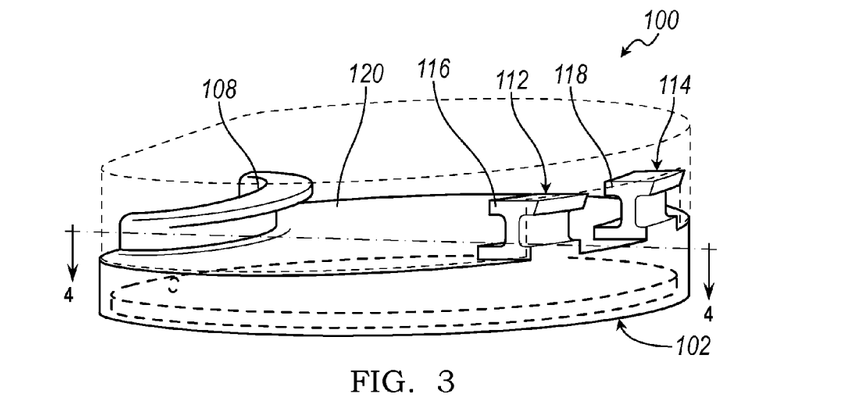
FIG. 3 is a proximal tibial prosthesis assembly, according to various embodiments.
Figure 4:
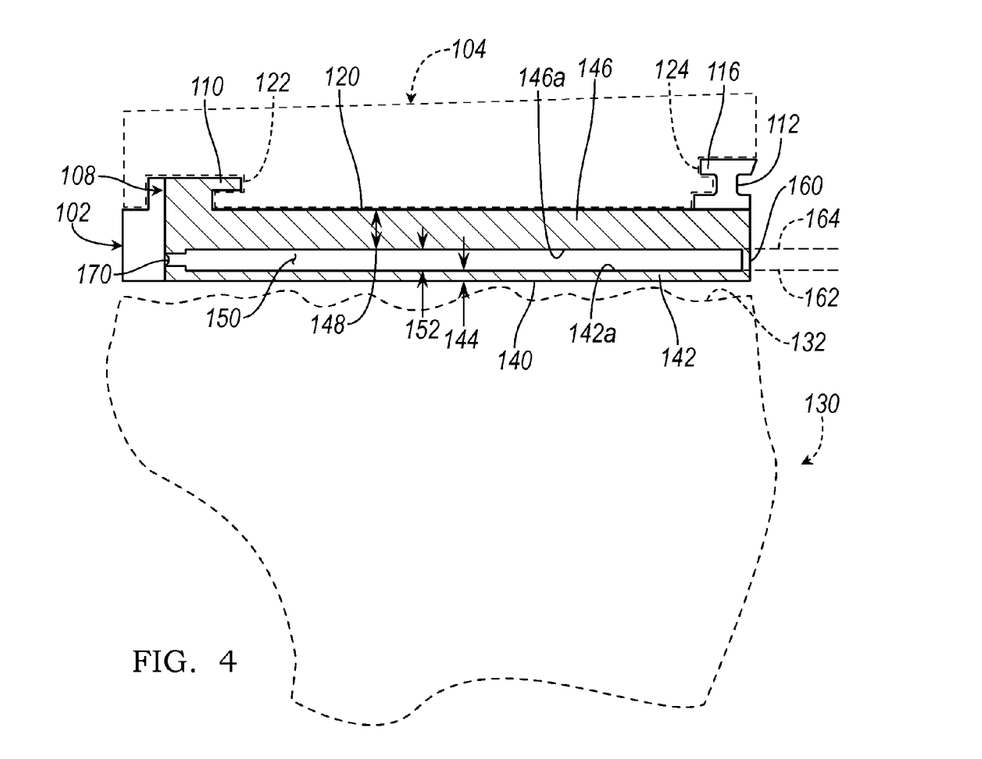
FIG. 4 is a cross-section of the tibial prosthesis of FIG. 3 taken along the line 4-4.

With reference to FIGS. 3 and 4, a tibial tray prosthesis assembly 100 is illustrated. The tibial prosthesis 100 can be similar to the Vanguard® Knee System sold by Biomet, Inc. It is understood that a knee system can further include a distal femoral prosthetic member that can engage a distal femur to articulate with the tibial prosthesis assembly 100. The tibial prosthesis assembly 100 can include a tibial tray member or portion 102 and a bearing member 104. The tibial tray member 102 can further include various engaging portions to engage the bearing member 104. For example, a posterior engagement portion or ledge 108 can include a finger or engagement ledge 110 to engage the bearing member 104. Additionally, anterior engagement fingers or portions 112 and 114 can further include engagement ledges or fingers 116 and 118 to engage the bearing member 104. It is further understood that the various locking bars or members, not specifically illustrated, can be provided to interconnect the bearing member 104 with the tibial tray portion 102.

Generally, an upper surface 120 of the tray member 102 can be polished, such as with a mirror polished surface to contact the bearing member 104. The bearing member 104 can further include cut-outs or receiving grooves 122 and/or 124 to engage or contact with the finger members 110 and/or

116, 118. The bearing member 104 can be held substantially immobile or be mobile relative to the tibial tray 102. The bearing member 104 can be formed of an appropriate material, such as a polymer material including the high molecular weight polyethylene as discussed above for the bearing portion 30. Further, the tibial tray member 102 can be formed of appropriate materials, such as metals, polymers, or other appropriate materials similar to the prosthesis 20 as discussed above.

The tibial tray 102 can be positioned against a tibia 130 as illustrated in phantom in FIG. 4. The tibia can include a proximal surface 132 that is prepared or partially prepared to receive the tibial tray 102. As is understood to one skilled in the art, the proximal tibial surface 132 can generally be substantially resected to provide a substantially smooth or flat surface for engagement with a tibial tray. Alternatively, the proximal surface 132 can be resected to only remove disease or a selected minimal amount of bone such that the surface is not completely flat for engagement with an external surface 140 of the tibial tray 102. The external surface 140 can be an external surface of a bottom or external wall 142 that can have a thickness 144. The tibial tray 102 can further have a second or upper wall 146 that has a second thickness 148. The first wall 142 can have a first internal surface 142a and the second wall 146 can have a second internal surface 146a. Defined between the surfaces 142a and 146a can be a void 150. A dimension 152 of the void 150 between the first surface 142a and the second surface 146a can be initially provided and can be selected to allow for deformation of the external wall 142 into the void 150, as discussed further herein.

As discussed above, the void 150 can allow for deformation of the external wall 142 into the void when contacting the surface 132 of the tibia 130. The external wall 142 can deform into the void 150 when contacting the surface 132 with an appropriate force. Specifically, the surface 142a moves into at least a portion of the initial volume of the void 150.

An outer edge or wall 160 can be provided with an appropriate thickness and dimension and may be substantially rigid during contacting of the external wall 142 with the upper tibial surface 132. As discussed above, regarding the upper rim wall 24 of the acetabular prosthesis 20 the exterior wall 160 of the tibial tray 102 can be substantially rigid so as to not move or change dimensions (i.e. deform) when contacting the tibia 130 to deform the external wall 142. For example, the external or perimeter wall 160 can extend from the exterior surface 140 to first region 162 that is generally equivalent with the inner surface 142a and then to a second region 164 that is generally equivalent with the second inner surface 146a. Accordingly, the external wall 160 may be provided to at least be substantially rigid for the area between the first region 162 and the second region 164. Thus, the external wall 142 can deform into the void 150 while the external wall 160 maintains substantially rigid and undeformed.

Additionally, a connection 170 can be provided to allow for connection of a supply, such as a material supply as discussed above. A material can be placed within the void 150 to allow for a physical contact between the first surface 142a and the second surface 146a to provide additional rigidity when the external wall 142 is deformed into the void 150. It is understood, however, that filling the void 150 with a material is not required.

It is further understood that the tibial tray prosthesis 102 can be formed in a manner similar to the acetabular prosthesis 20 discussed above. In particular, the first wall 142 and the second wall 146 can be formed separately from the external perimeter wall 160. All three of the walls 142, 146, and 160 can then be connected together with an appropriate connection mechanism such as welding, brazing, adhesives, or other appropriate connection mechanism. Moreover, the external perimeter wall 160 can be formed with at least one of the first wall 142 or the second wall 146 and the other of the first wall 142 or the second wall 146 can be connected thereto. Alternatively, all of the walls 142, 146, and 160 can all be formed as a single piece to provide the tibial tray prosthesis 102. Regardless of the mechanism for providing the tibial tray 102, the wall 142 is generally provided to deform relative to the tibial surface 132 such that at least the external surface 140 of the external wall 142 will conform, such as mirror, the shape and geometry of the tibial surface 132.

Figure 5:
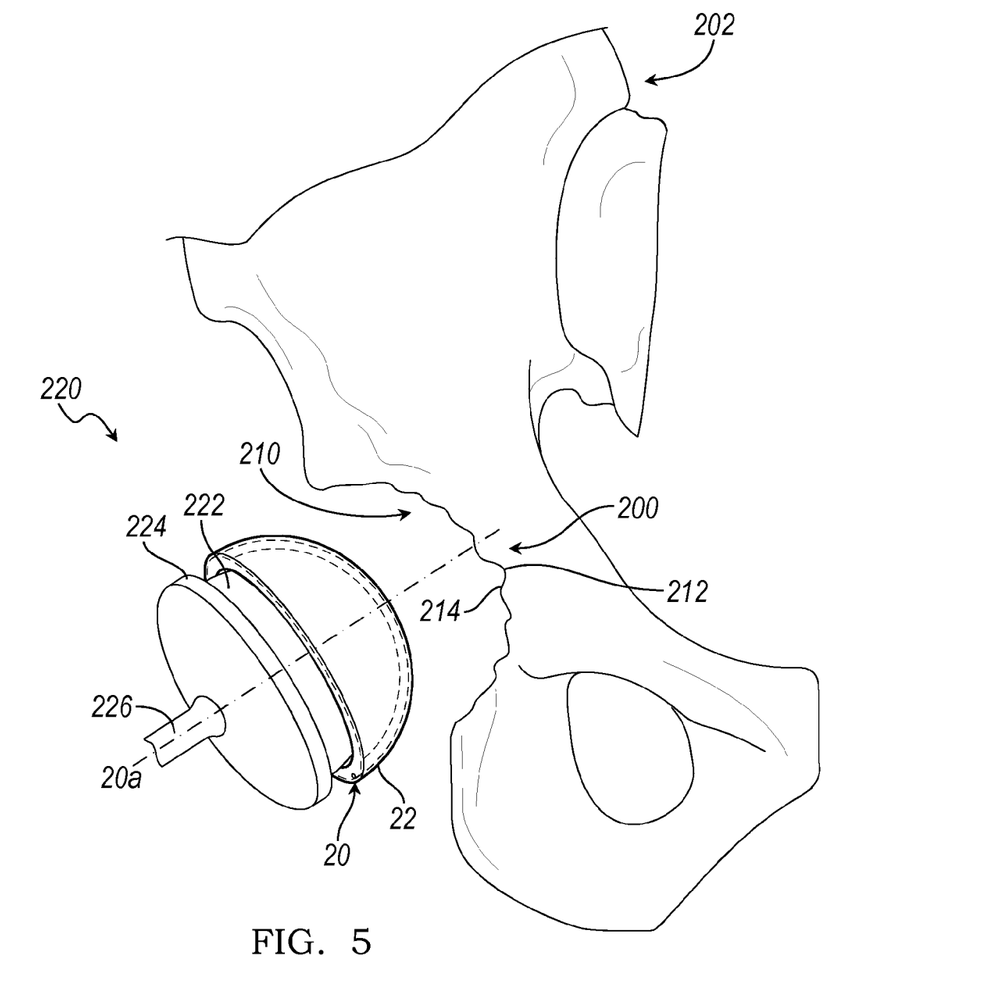
FIG. 5 is an environmental view of the acetabular prosthesis of FIG. 1.
Figure 6:
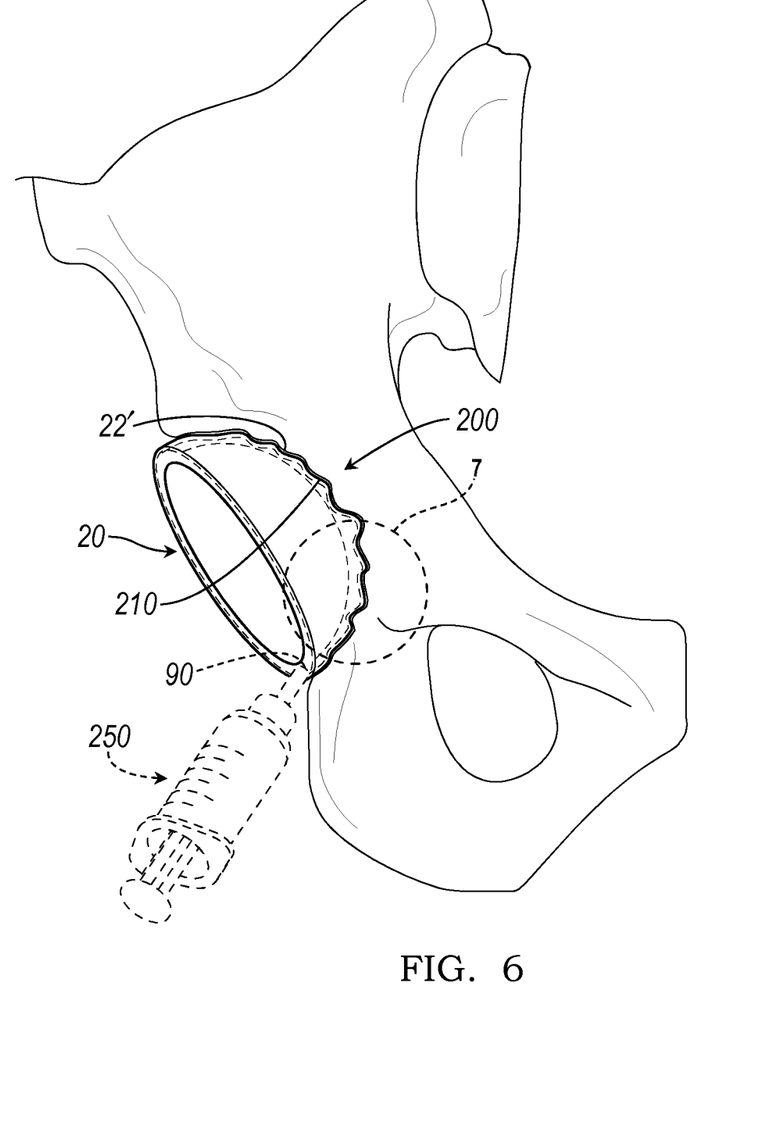
FIG. 6 is an implanted environmental view of the acetabular prosthesis of FIG. 1.
Figure 7:
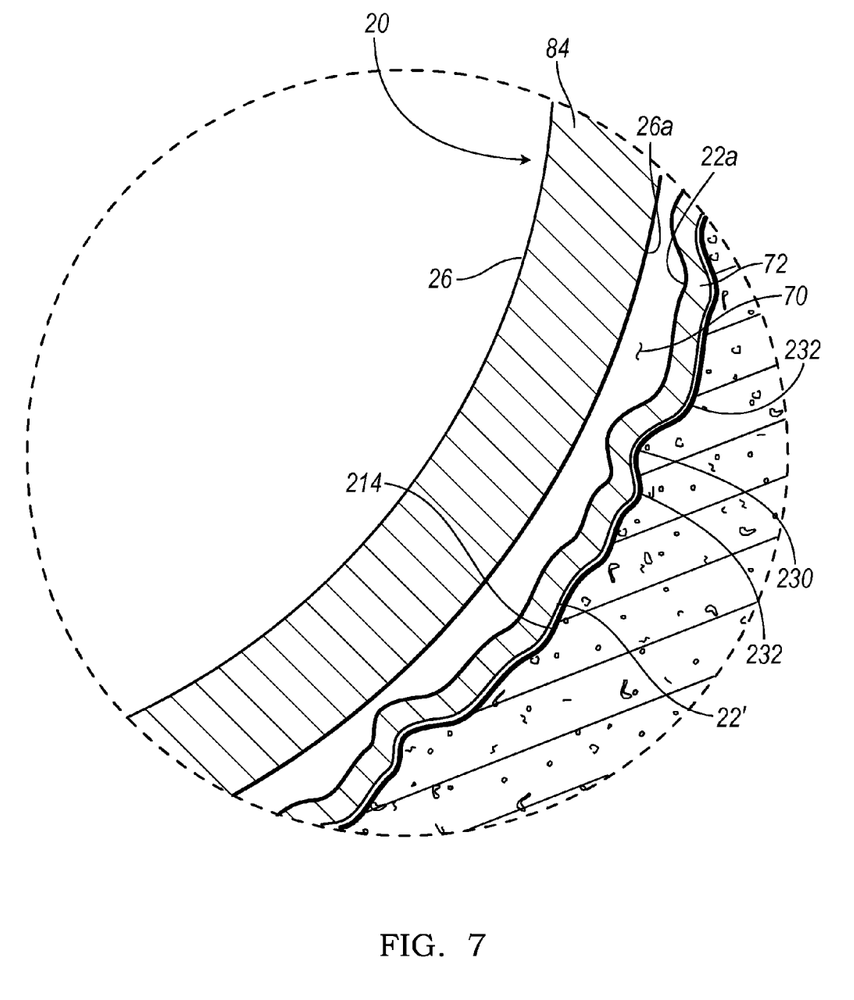
FIG. 7 is a detailed cross-sectional view of the implanted acetabular prosthesis taken from FIG. 6.

Returning reference to FIGS. 1 and 2 and with additional reference to FIGS. 5-7, the acetabular prosthesis 20 can be positioned within an acetabulum 200 of a pelvis 202 of a selected patient. The acetabulum 200 can be prepared to receive the acetabular prosthesis 20 according to any appropriate procedure. For example, a user, such as a surgeon, can prepare the acetabulum 200 by removing selected portions of the acetabulum 200. However, a reamer and/or other bone removal tools may not be required to form a substantially smooth or congruent surface of the acetabulum 200. A prepared smooth surface is a surface that has only minor variations from a single line. The acetabulum 200 can, however, have a prepared surface 210 that is not substantially smooth or perfectly curved.

The prepared surface 210 of the acetabulum 200 can include valley or depression regions 212 and peak regions 214. The valley regions 212 and the peak regions 214 can be understood to be formed along the entire three-dimensional surface or region of the acetabulum 200, and is illustrated in two dimensions in FIG. 5 simply for the current discussion. The prepared acetabular surface 210, therefore, can contact the external surface 22 of the acetabular prosthesis 20 when the acetabular prosthesis 20 is positioned into the acetabulum 200. An appropriate implantation tool 220 can be used to position the acetabular prosthesis 20 into the prepared acetabulum 200. The implantation tool 220 can be any appropriate configuration. For example, the implantation tool can include an internal surface contacting region 222 and a rim contacting region 224 that is interconnected with a handle or elongated member 226. Various impaction instruments, such as a hammer, can be used to impact the acetabular prosthesis 20 into the acetabulum 200. An appropriate force can be provided through the implantation tool 220 to impact the acetabular prosthesis 20 into the prepared acetabulum 200.

Turning reference to FIGS. 6 and 7, the impacted or placed acetabular prosthesis 20 once positioned within the prepared acetabulum 200 can include an external deformed surface 22' that can substantially conform or match the shape (e.g. form a mirror match) of the prepared acetabular surface 210. The deformation of the external surface 22' can be substantially identical or may closely match the prepared acetabular surface 210. For example, a gap or space between the prepared acetabular surface 210 and the external surface 22' can generally be less than about 0.5 mm, including about 1.5 mm. It is understood that the external conformed surface 22' would be substantially deformed to match the shape of the prepared acetabular surface 210 and need not include a perfect or smooth arc or curved surface from one rim portion to another rim portion going through a central axis 20a of the acetabular prosthesis 20.

With particular reference to FIG. 7, the peak region 214 can engage the exterior surface 22' to deform the exterior surface 22' into the void 70 of the acetabular prosthesis 20. The bone peak 214 can form a valley 230 in the deformed external surface 22'. The valley 230 can also be a depression that is substantially a point depression within the external wall 72 of the acetabular prosthesis 20. The depression or valley 230 can be surrounded or adjacent to peak regions 232 and 234. The void 70 allows the external wall 72 to be deformed into the void 70 while allowing the wall 84 and/or the interior surface 26 of the acetabular prosthesis 20 to remain substantially unchanged such that the inner wall 84 is substantially not deformed. In other words, the inner wall 84 and/or the surface 26 remain substantially in an original or provided configuration. The internal surface 26, as discussed above, is configured, such as with an initial configuration, to contact the bearing member 30. Accordingly, the bearing member 30 is formed to have a surface that engages the internal surface 26 of the acetabular prosthesis 20 in a selected manner. Maintaining the internal surface 26 in a non-deformed configuration, therefore, allows for the internal surface 26 to receive the bearing member 30 in an appropriate manner for replacing the acetabulum 200 of the patient. The outer wall 72 and/or the surface 22' may be irreversibly or plastically deformed.

Regarding reference to FIG. 6, a supply 250 can engage the connection 90 to fill the void 70 with a selected material, such as a bone cement material. The bone cement can be any appropriate polymerizing or hardening material that can fill the void 70 and provide a physical rigidness between the inner surface 26a and the inner surface 22a. The additional rigidity can assist in maintaining the shape of the external wall 72 once the acetabular prosthesis 20 is implanted in to the acetabulum 200. Accordingly, the initially deformed shape of the external wall 72 can be maintained for the life of the acetabular prosthesis 20.

It is further understood that the tibial tray prosthesis 100 can be implanted and the external wall 142 can be deformed in a manner similar to the acetabular prosthesis 20, as illustrated in FIGS. 6 and 7 for the acetabular prosthesis 20. It is further understood that selected additional prosthetic members, such as glenoid prostheses, and other prosthetic members can also include walls that can be deformed when contacting or engaged into the anatomy of a subject. Accordingly, the exemplary embodiments of an acetabular prosthesis 20 and the tibial tray prosthesis 102 are merely exemplary and not the limiting examples. Additionally, it is understood that the external surface of an appropriate prosthetic member can engage a substantially smooth or fully resected receiving surface, such as a fully reamed acetabulum 200. The external wall may deform, even if to a lesser degree than illustrated above, when the acetabulum or other appropriate surface is completely resected or reamed to prepare the selected surface, for implantation of a prosthetic member. The deformation of the external wall may still allow for a greater contact of the prosthetic member with the surface, prepared to any extent or with no preparation to assist in maintaining and achieving a greater longevity of the prosthetic member, reduced possibility of loosening of the prosthetic member, and a reduced possibility or requirement for revision procedure in the future. Additionally, the deformation can allow for greater loading of the contacted bone to assist in resisting resorption of the bone and assist in allowing bone growth and/or bone ingrowth into the prosthetic member after implantation.

The prosthesis, according to the various disclosed embodiments, can be formed without seams, such as formed as a single member with an internal void. Thus, the wall may be formed as a continuous portion. Further, the prosthesis formed with a deformable wall can be provided in a single size to fit a broader range of patient sizes. For example, a single prosthesis need not be provided for multiple joint gaps, thicknesses, etc. This can also reduce inventory of a supplier, such as a hospital inventory, and related costs. Moreover, the deformation allows for variability of an individual prosthetic member, thus user selection of a single prosthetic member can be more variable and allow greater intra-procedure customization by a user, such as a surgeon. Also, a limiting feature can be provided to limit or eliminate deformation. Thus, a user can select to engage the limiting feature to limit or elimination deformation of a prosthetic member, for selected purposes.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A prosthesis for placement in an anatomy, comprising:
   an interior wall having an interior wall outer surface and an interior wall inner surface;
   an exterior wall having an exterior wall outer surface and an exterior wall inner surface, wherein at least a portion of the interior wall inner surface faces at least a portion of the exterior wall inner surface;
   a connecting wall connecting the interior wall and the exterior wall, wherein the connecting wall is rigid relative to at least the exterior wall, wherein:
      the interior wall is spaced apart from the exterior wall to define a void between the interior wall inner surface and the exterior wall inner surface;
      the interior wall is rigid relative to the exterior wall;
      the exterior wall is configured to deform into the void when forced against a non-smooth anatomical surface, forming a deformed exterior wall, such that the exterior wall outer surface of the deformed exterior wall comprises a non-smooth surface; and
   a strengthening material operable to be placed within the void defined by the interior wall and the deformed exterior wall.

2. The prosthesis of claim 1, wherein the interior wall has a first thickness greater than a second thickness of the exterior wall.

3. The prosthesis of claim 1, further comprising:
   a bearing member configured to be implanted adjacent to the interior wall outer surface.

4. The prosthesis of claim 1, wherein the exterior wall outer surface is configured to contact a non-smooth prepared acetabulum.

5. The prosthesis of claim 1, wherein the exterior wall outer surface is configured to contact a non-smooth prepared proximal tibia.

6. A prosthesis for placement in an anatomy, comprising:
   an interior wall;
   an exterior wall spaced apart from the interior wall, wherein the interior wall is rigid relative to the exterior wall;

a connecting wall connecting the interior wall and the exterior wall, wherein the connecting wall is rigid relative to at least the exterior wall;

a void bound by the interior wall, the exterior wall, and the connecting wall, wherein the exterior wall is configured to deform into the void when forced against an anatomical surface, forming a deformed exterior wall with a non-smooth surface; and a filling material configured to be placed within the void defined by the interior wall, the connecting wall, and the deformed exterior wall.

7. The prosthesis of claim 6, wherein when the exterior wall deforms into the void the interior wall remains in an initial configuration.

8. The prosthesis of claim 6, wherein the exterior wall is configured to plastically deform into the void.

9. The prosthesis of claim 6, wherein the exterior wall is thinner than the interior wall at least at a contact region with the anatomical surface.

10. The prosthesis of claim 6, wherein the interior wall is configured to engage a bearing member.

11. The prosthesis of claim 10, wherein the bearing member is configured to articulate with at least one of a femoral prosthesis, a tibial prosthesis, or a humeral prosthesis.

12. A method of providing a prosthesis for placement in an anatomy, comprising:

providing an interior wall having an interior wall outer surface and an interior wall inner surface;

providing an exterior wall having an exterior wall outer surface and an exterior wall inner surface, wherein the interior wall is rigid relative to the exterior wall, wherein at least a portion of the interior wall inner surface faces at least a portion of the exterior wall inner surface;

providing a connecting wall portion connecting the interior wall and the exterior wall, wherein the connecting wall is rigid relative to at least the exterior wall;

providing the interior wall spaced apart from the exterior wall to define a void between the interior wall inner surface and the exterior wall inner surface;

configuring the exterior wall portion to deform into the void, forming a deformed exterior wall, when forced against a non-smooth anatomical surface such that the exterior wall outer surface of the deformed exterior wall comprises a non-smooth surface; and providing a strengthening material within the void defined by the interior wall and the deformed exterior wall.

13. The method of claim 12, wherein providing the exterior wall includes forming the exterior wall to plastically deform into the void after being forced against the anatomical surface.

14. The method of claim 13, wherein providing the interior wall includes providing the interior wall to maintain an original configuration after the exterior wall has plastically deformed.

15. The method of claim 12, wherein providing the interior wall, providing the exterior wall, and providing the connecting wall includes forming each of the interior wall, the exterior wall, and the connecting wall separately and connecting each of the interior wall, the exterior wall, and the connecting wall together.

* * * * *